United States Patent
Kozak et al.

(10) Patent No.: US 8,126,536 B2
(45) Date of Patent: Feb. 28, 2012

(54) METHOD AND APPARATUS FOR DETERMINING THE FRONTAL PLANE OF THE PELVIC BONE

(75) Inventors: Josef Kozak, Tuttlingen (DE); Peter Keppler, Ulm (DE)

(73) Assignees: Aesculap AG, Tuttlingen (DE); Universitaet Ulm, Ulm (DE)

( * ) Notice: Subject to any disclaimer, the term of this patent is extended or adjusted under 35 U.S.C. 154(b) by 457 days.

(21) Appl. No.: 12/231,883

(22) Filed: Sep. 4, 2008

(65) Prior Publication Data

US 2009/0101158 A1 Apr. 23, 2009

(30) Foreign Application Priority Data

Oct. 17, 2007 (DE) .................. 10 2007 049 671

(51) Int. Cl.
*A61B 5/00* (2006.01)
(52) U.S. Cl. .................. 600/424; 600/437; 606/130
(58) Field of Classification Search .................. 600/407, 600/424–429, 437; 606/130
See application file for complete search history.

(56) References Cited

U.S. PATENT DOCUMENTS

| | | | | |
|---|---|---|---|---|
| 5,966,827 A * | 10/1999 | Horvath et al. | ................ | 33/512 |
| 6,621,247 B1 * | 9/2003 | Bulling et al. | ................ | 320/116 |
| 6,669,653 B2 * | 12/2003 | Paltieli | ................ | 600/588 |
| 2002/0077540 A1 | 6/2002 | Kienzle, III | | |
| 2004/0254584 A1 * | 12/2004 | Sarin et al. | ................ | 606/151 |
| 2004/0254586 A1 * | 12/2004 | Sarin et al. | ................ | 606/130 |
| 2005/0203540 A1 * | 9/2005 | Broyles | ................ | 606/102 |
| 2006/0004284 A1 | 1/2006 | Grunschlager et al. | | |
| 2006/0095047 A1 | 5/2006 | de la Barrera | | |
| 2008/0132783 A1 | 6/2008 | Revie et al. | | |
| 2008/0214932 A1 * | 9/2008 | Mollard et al. | ................ | 600/429 |
| 2008/0269757 A1 * | 10/2008 | McMinn | ................ | 606/87 |
| 2009/0105714 A1 * | 4/2009 | Kozak | ................ | 606/102 |
| 2009/0171370 A1 * | 7/2009 | Yoon et al. | ................ | 606/130 |
| 2009/0306679 A1 * | 12/2009 | Murphy | ................ | 606/130 |
| 2010/0030231 A1 * | 2/2010 | Revie et al. | ................ | 606/130 |

FOREIGN PATENT DOCUMENTS

| | | |
|---|---|---|
| DE | 103 11 454 | 10/2004 |
| DE | 103 49 938 | 6/2005 |
| DE | 202005009777 | * 1/2006 |
| DE | 10 2005 003 317 | 7/2006 |
| DE | 11 2005 002 453 | 8/2007 |
| EP | 0 944 354 | 9/1999 |
| EP | 1 611 863 | 1/2006 |
| WO | 2004/030556 | 4/2004 |
| WO | 2005/084541 | 9/2005 |

* cited by examiner

*Primary Examiner* — Brian Casler
*Assistant Examiner* — Amanda Lauritzen
(74) *Attorney, Agent, or Firm* — Lipsitz & McAllister, LLC

(57) ABSTRACT

In a method for determining the pelvic inlet plane of the pelvic bone, which is defined by the following three points of the pelvic bone:
point A: spina iliaca anterior superior left
point B: spina iliaca anterior superior right
point C: symphysis pubis,
by non-invasive determination of the position of one of the two points A or B and point C, in order to also be able to carry out this determination whenever point A or point B is not accessible, it is proposed that the position of the following points of the pelvic bone be additionally determined non-invasively:
point D: spina iliaca posterior superior left
point E: spina iliaca posterior superior right,
and that the position of the pelvic inlet plane be calculated from the position of the non-invasively determined points A or B, C, D and E.

18 Claims, 3 Drawing Sheets

METHOD AND APPARATUS FOR DETERMINING THE FRONTAL PLANE OF THE PELVIC BONE

The present disclosure relates to the subject matter disclosed in German application number 10 2007 049 671.2 of Oct. 17, 2007, which is incorporated herein by reference in its entirety and for all purposes.

BACKGROUND OF THE INVENTION

The invention relates to a method for determining the pelvic inlet plane of the pelvic bone, which is defined by the following three points of the pelvic bone:
point A: spina iliaca anterior superior left
point B: spina iliaca anterior superior right
point C: symphysis pubis
by non-invasive determination of the position of one of the two points A or B and point C. The invention also relates to an apparatus for performing this method.

When inserting implants and performing other operations, it is often necessary to describe the anatomical conditions in an abstract manner in order to record the anatomical conditions in mathematical models, for example, in connection with known navigation systems and with the processing of the thereby obtained data in data processors.

For example, it is known (DE 10 2005 003317 A1) to describe the pelvic bone by defining a pelvic inlet plane, which is defined by three prominent points of the pelvic bone, namely the following points:
point A: left spina iliaca anterior superior (left anterior superior iliac spine)
point B: right spina iliaca anterior superior (right anterior superior iliac spine)
point C: symphysis pubis (pubic symphysis).

For example, these prominent points may be percutaneously palpated. It is also possible to non-invasively determine these points in some other way, for example, by an ultrasonic sensor, by X-rays or by other imaging methods, for example, computed tomography methods.

In all cases, the prominent points can be used to describe the pelvic inlet plane and, therefore, this pelvic inlet plane can be used to calculate the position of the pelvic bone in subsequent computations.

However, a precondition for this method is that the three prominent points be accessible, for example, during percutaneous palpation or when a preferably navigated ultrasonic sensor is used. However, this is not possible in all cases, for example, when a patient is lying on his side on an operating table only one of the points A or B is accessible, i.e., either the left or the right spina iliaca anterior superior only. It is, therefore, impossible to determine the pelvic inlet plane in this special position of the patient.

An object of the invention is to indicate a method by means of which, in these cases, too, where one of the points A and B is not accessible, the pelvic inlet plane can be determined.

SUMMARY OF THE INVENTION

This object is accomplished, in accordance with the invention, in a method of the kind described at the outset, in that the position of the following points of the pelvic bone is additionally determined non-invasively:
point D: spina iliaca posterior superior left (left posterior superior iliac spine)
point E: spina iliaca posterior superior right (right posterior superior iliac spine),
and in that the position of the pelvic inlet plane is calculated from the position of the non-invasively determined points A or B, C, D and E.

Accordingly, the determination of the missing point A or B, which is not possible, is replaced by the determination of additional points, namely points D and E, which is also possible in the patient's lateral position, and the position data of the pelvic inlet plane can be calculated from these points by certain calculation methods. In doing so, it is to be assumed that geometrical relationships exist between the position of points D and E, on the one hand, and the position of points A and B, on the other hand, on the pelvic bone, which are very similar or identical in the pelvic bone of all patients.

The non-invasive determination of the position data of the described points can be achieved by, for example, percutaneous palpation. This palpation may also be carried out with the aid of a navigated palpation instrument. Another possibility is to determine the position by means of a navigated ultrasonic sensor. It is also possible to use other methods for non-invasively determining bony structures, with which one skilled in the art is familiar, for example, imaging methods with X-rays or by nuclear magnetic resonance.

In a first preferred embodiment of the invention, in order to calculate the position of the pelvic inlet plane, the vector between points D and E is displaced parallel to itself so that it passes through the non-invasively determined point A or B, and the pelvic inlet plane is determined as the plane which is defined by the vector between the non-invasively determined point A or B and point C and by the vector starting from the non-invasively determined point A or B and running parallel to the vector between points D and E.

Accordingly, it is assumed that the connecting vector between points D and E, on the one hand, and points A and B, on the other hand, run essentially parallel in all patients, so that by displacing the vector connecting points D and E into the non-invasively determined point A or B, this vector is displaced into the pelvic inlet plane. Hence the position data of the pelvic inlet plane can be determined by this vector and the connecting vector between the non-invasively determined point A or B and point C.

In this method, it is not necessary to know the exact position of the inaccessible and non-determinable point B or A, as the pelvic inlet plane can be adequately determined solely by the arrangement of the two vectors.

Nor is it of importance whether the vector displaced parallel to the vector between points D and E starts from the non-invasively determined point A or B or simply passes through it; it is only essential that this non-invasively determined point A or B should lie on this displaced vector.

In a modified method, in order to calculate the position of the unknown point B or A, the vector between points D and E is displaced so that it starts from the non-invasively determined point A or B and points towards the unknown point B or A, the length of the vector is multiplied by a factor that increases it, and the tip of the thus increased vector is assumed as position of the unknown point B or A. In this method, it is assumed, firstly, that the direction of the vector between points D and E and of the vector between points A and B is parallel, and, secondly, that certain length relationships exist between these vectors, which have a very similar or even the same value for a large number of patients, and, therefore, conclusions may be drawn from the distance between points D and E as to the distance between points A and B.

This factor may have a fixed value which is, for example, between 2.8 and 2.5. This value may differ for males and females; for example, the value for males may be between 2.8 and 2.75, for females between 2.63 and 2.58.

In another method, this factor is determined by the distance vector of the non-invasively determined point A or B and point C being projected onto the displaced vector, and by the projected distance along the displaced vector being doubled. In this method, it is assumed that the pelvis is of symmetrical configuration on either side of the symphysis pubis, and, therefore, the length of the connecting vector between points A and B is twice the distance between the non-invasively determined point A or B, on the one hand, and the projection of the symphysis pubis onto this vector, on the other hand.

In both methods, it is possible, without knowledge of one of points A or B, to determine its position relatively accurately, and, therefore, the pelvic inlet plane can also be determined from the three points A, B and C without being able to directly determine the position data of one of points A and B.

A further object of the invention is to provide an apparatus for performing this method.

This object is accomplished, in accordance with the invention, by an apparatus for determining the frontal plane of the pelvic bone, which is defined by the following three points of the pelvic bone:

point A: spina iliaca anterior superior left (left anterior superior iliac spine)
point B: spina iliaca anterior superior right (right anterior superior iliac spine)
point C: symphysis pubis (pubic symphysis),
comprising a navigation system, a navigated position sensor for points A, B and C and for the following further points:
point D: spina iliaca posterior superior left (left posterior superior iliac spine)
point E: spina iliaca posterior superior right (right posterior superior iliac spine),
and a data processor which is programmed so as to calculate the position of the pelvic inlet plane from the position data of points A or B, C, D and E.

The position sensor may be a palpation instrument, in particular, a navigated palpation instrument, an ultrasonic sensor, in particular, a navigated ultrasonic sensor or any other instrument which enables non-invasive or possibly also invasive detection of the position of points A, B, C, D and E, insofar as these are accessible in view of the patient's position.

In order to calculate the position of the pelvic inlet plane, the data processor may be programmed so as to displace the vector between points D and E parallel to itself so that it passes through the non-invasively determined point A or B, and so as to calculate the pelvic inlet plane as the plane which is defined by the vector between the non-invasively determined point A or B and point C and by the vector starting from the non-invasively determined point A or B and running parallel to the vector between points D and E.

In another embodiment of the invention, in order to calculate the position of the unknown point B or A, the data processor may be programmed so as to displace the vector between points D and E so that it starts from the non-invasively determined point A or B and points in the direction of the unknown point B or A, so as to multiply the length of the vector by a factor that increases it, and so as to assume the tip of the thus increased vector as position of the unknown point B or A.

In both cases, it is assumed that the vector connecting points A and B and the vector connecting points D and E run approximately or exactly parallel in different patients. In the case of the first type of programming, the pelvic inlet plane is determined without detecting the position of the non-determinable point B or A; in the subsequently described method, however, it is also possible to calculate the position of this second point B or A which is not directly determinable.

In this method, to increase the vector, the data processor uses a factor which starts from the non-invasively determined point A or B and runs parallel to points D and E. This factor may have a fixed value which, in particular, is between 2.8 and 2.5.

This value may differ in males and females, for example, in males it may be between 2.8 and 2.75, in females between 2.63 and 2.58.

The data processor may, however, also be programmed so that the factor is determined by the distance vector of the non-invasively determined point A or B and point C being projected onto the displaced vector, and by the projected distance along the displaced vector being doubled. In this case, it is assumed that the pelvic bone is built symmetrically in relation to the central position defined by the symphysis pubis.

The following description of preferred embodiments of the invention serves in conjunction with the drawings for a more detailed explanation.

DETAILED DESCRIPTION OF THE INVENTION

Figure 1:
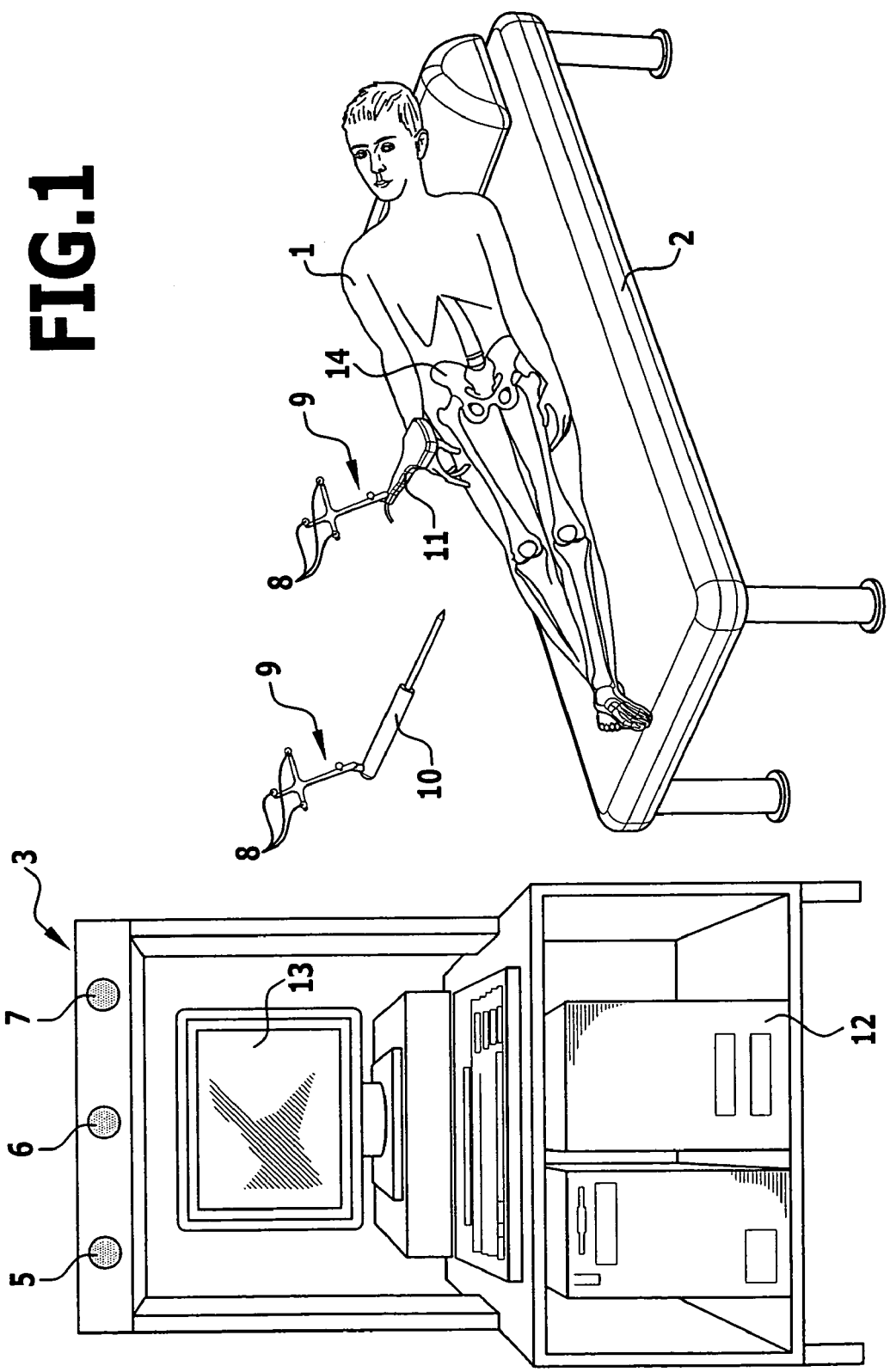
FIG. 1 shows a schematic representation of a patient lying on his side and a navigation system for detecting the position of navigated position sensors.

There is shown in FIG. 1 a patient 1 lying on his side on an operating table 2. Operations may be carried out on the patient in this position. Located beside the operating table 2 is a navigation system 3 with a number of radiation emitters 5, 6, 7, which at the same time are also configured as radiation receivers. The emitted radiation may be infrared radiation.

This radiation is reflected by reflective surfaces 8, which may be spheres arranged as markers 9 on various instruments 10, for example, a palpation instrument 10 and an ultrasonic sensor 11. The navigation system is thus able to detect in a manner known per se the position of the instruments in space, i.e., their exact position and their orientation.

A data processor 12 with a display device 13, in the form of a monitor in the embodiment shown, is also associated with the navigation system 3.

Figure 2:
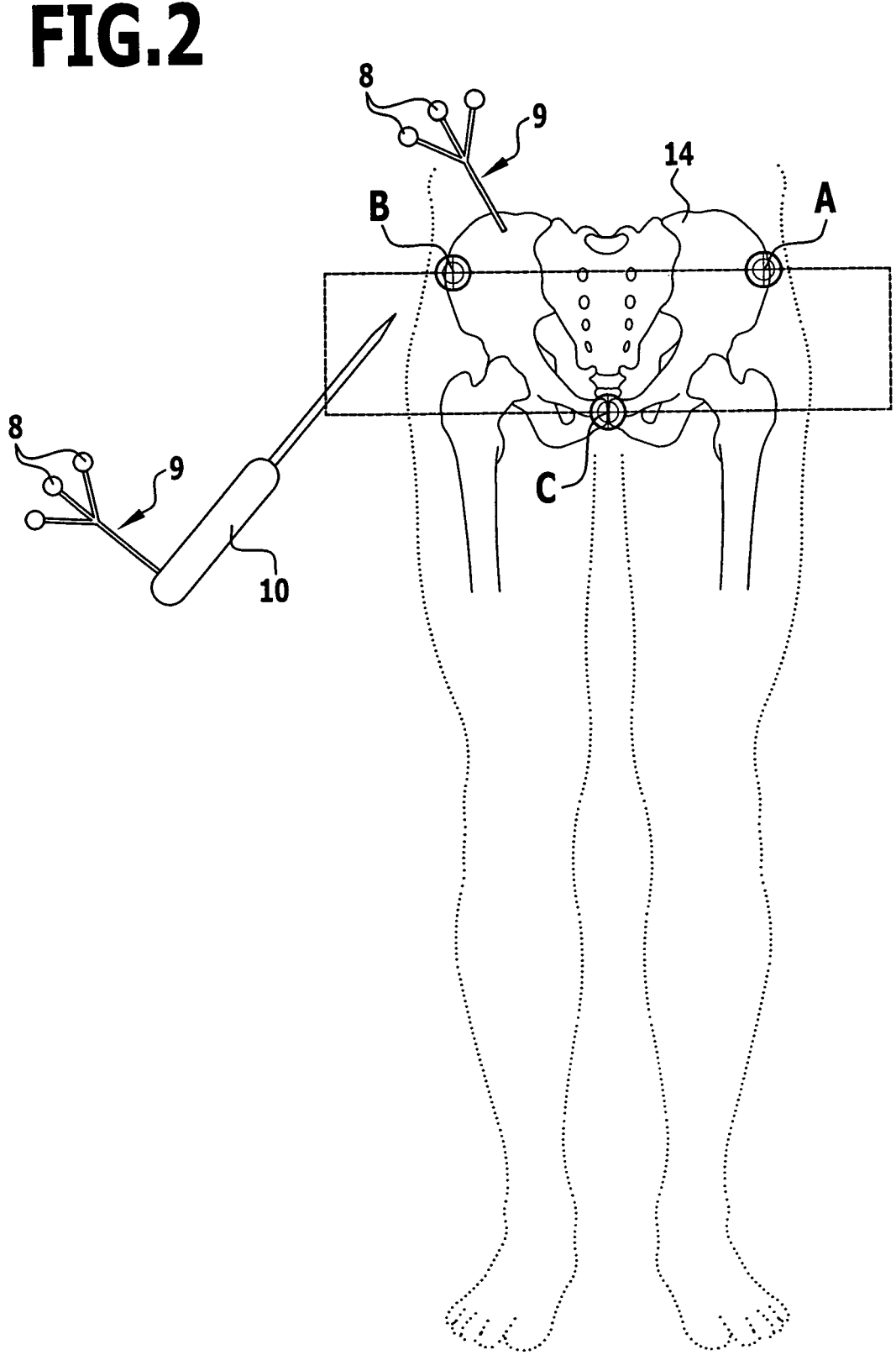
FIG. 2 shows a schematic front view of a patient with points A, B and C defining the pelvic inlet plane.

Three prominent points of the pelvic bone, which define a so-called pelvic inlet plane 15 (FIG. 2), are used to enable the position of a patient's pelvic bone 14 to be described. These prominent points are the following points:

point A: spina iliaca anterior superior left (left anterior superior iliac spine)
point B: spina iliaca anterior superior right (right anterior superior iliac spine)
point C: symphysis pubis (pubic symphysis)

These three points may be palpated percutaneously, for example, by hand or with the aid of the navigated palpation instrument 10. It is also possible to detect these points with the aid of the navigated ultrasonic sensor. In any case, it is in this way possible to locate the position of the three points A, B and C in space, and the navigation system can forward a set of data corresponding to the position of points A, B and C to the data processor 12. The precondition for this is, however, that all three points A, B and C be freely accessible. This is not the case in the lateral position shown in FIG. 1, where only two of the three points can be determined in the described manner, namely either point A or point B and, in addition, in any case, point C.

Accordingly, it is initially not possible to determine the pelvic inlet plane on patients lying in lateral position.

For this reason, the surgeon determines in addition to the two determinable points A or B and C two further prominent points of the pelvic bone 14, namely the following points:
point D: spina iliaca posterior superior left (left posterior superior iliac spine)
point E: spina iliaca posterior superior right (right posterior superior iliac spine).

On a patient lying on his side, these two prominent points can be readily located on his back by palpation or with the aid of an ultrasonic probe, etc.

Accordingly, after such a measurement, the following points: A, C, D and E or B, C, D and E are available for calculation of the pelvic inlet plane. The points D and E do not lie in the pelvic inlet plane, but they can be used in accordance with the method described hereinbelow to determine the position of the pelvic inlet plane or the missing point B or A in the pelvic inlet plane with respect to its position.

To do so, the vector that connects points D and E is first determined by the data processor. This vector is designated by reference numeral 16 in FIG. 3. This vector 16 is displaced parallel to itself, more specifically, in a first method, so that this parallel displaced vector passes through the non-invasively determined point A or B.

This thus determined vector and the vector connecting the non-invasively determined point A or B and point C together define a plane, and this plane is the pelvic inlet plane that is sought after. Accordingly, the data processor can calculate from these two vectors the position of the pelvic inlet plane. The position of the pelvic inlet plane is obtained as result, but not the exact coordinates of the inaccessible point B or A which is not determinable with respect to its position data.

Figure 3:
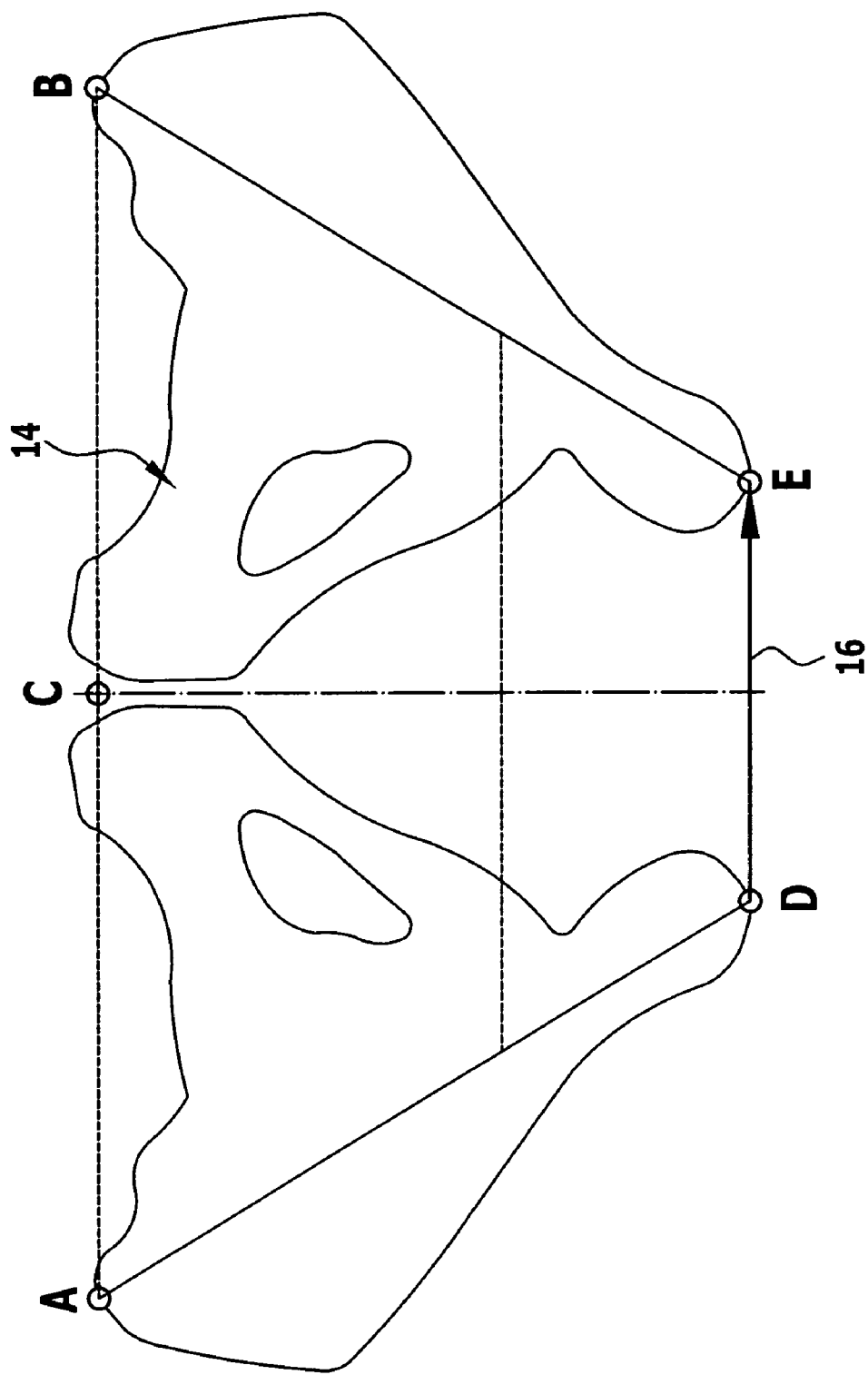
FIG. 3 shows a schematic sectional view of the pelvic bone in a view from above with the points A, B, C, D and E which are relevant for determining the pelvic inlet plane.

However, these data can be obtained in the following manner in another method:

As in the method described hereinabove, the vector connecting points D and E, i.e., the vector 16 in FIG. 3, is first determined by the data processor.

This vector 16 is displaced parallel to itself so that its initial point lies in point A or B, the position data of which it has been possible to determine. In addition, the vector 16 is optionally rotated through 180° so that its tip points in the direction of the respective other point B or A, the position data of which it has not been possible to determine.

Since the distance between points D and E is significantly smaller than the distance between points A and B, the vector 16 does point in the direction of point B or A, the position data of which it has so far not been possible to determine, but the tip is located at a distance from this point. Therefore, it is still necessary to modify the length of this displaced vector.

This may be done in various ways.

In a first method, it is assumed that there exists between the distance between points D and E, on the one hand, and points A and B, on the other hand, a fixed factor which is identical or similar for all pelvic bones of different patients. It has been found that this is approximately the case, this factor being different for males and females. In males this factor is approximately between 2.8 and 2.75, in females approximately between 2.63 and 2.58.

When such a factor is used to determine the distance between points A and B from the length of the vector 16, in practice, values are obtained where the standard deviation from the actual values of the distance between points A and B lies in the order of magnitude of between 10 and 15 mm; a relatively good approximation of the position of the third point of the pelvic inlet plane that is not directly determinable is thus obtained.

In a second method it is assumed that in each patient the pelvic bone 14 is symmetrical in relation to a perpendicular central plane which passes through the symphysis pubis. Therefore, the vector which connects the measured one of the two points A and B to point C is projected onto the vector which results from the displaced vector 16 and starts at the measured point A or B. Hence, owing to the assumed symmetry, the tip of the vector running from the measured point A or B to point C is projected onto the displaced vector in a point which corresponds to half of the distance between points A and B. It is now only necessary to double this distance in order to arrive at the non-determinable point B or A and so the position data of this point, too, are now available.

The invention claimed is:
1. A method for determining a pelvic inlet plane of a pelvic bone, the pelvic inlet plane being defined by the following three points of the pelvic bone:
point A denoting a left anterior superior iliac spine; point B denoting a right anterior superior iliac spine; and point C denoting a pubic symphysis,
the method comprising:
non-invasively determining a position of one of the two points A or B, the other of the two points B or A is unknown;
non-invasively determining a position of point C,
non-invasively determining a position of each of the following points of the pelvic bone:
point D denoting a left posterior superior iliac spine; and
point E denoting a right posterior superior iliac spine, and
calculating a position of the pelvic inlet plane from the positions of the non-invasively determined point A or B and of points C, D and E,
wherein in order to calculate the position of the pelvic inlet plane:
a vector between points D and E is displaced parallel to itself so that it passes through the non-invasively determined point A or B, and
the pelvic inlet plane is determined as the plane which is defined by a vector between the non-invasively determined point A or B and point C and by the displaced vector starting from the non-invasively determined point A or B which runs parallel to the vector between points D and E.

2. A method in accordance with claim 1, wherein the position of points A or B, C, D and E is determined by percutaneous palpation.

3. A method in accordance with claim 1, wherein the position of points A or B, C, D and E is determined by an ultrasonic examination.

4. A method for determining a pelvic inlet plane of a pelvic bone, the pelvic inlet plane being defined by the following three points of the pelvic bone:
point A denoting a left anterior superior iliac spine; point B denoting a right anterior superior iliac spine; and point C denoting a pubic symphysis,
the method comprising:
non-invasively determining a position of one of the two points A or B, the other of the two points B or A is unknown;
non-invasively determining a position of point C, non-invasively determining a position of each of the following points of the pelvic bone:
point D denoting a left posterior superior iliac spine; and
point E denoting a right posterior superior iliac spine, and
calculating a position of the pelvic inlet plane from the positions of the non-invasively determined point A or B and of points C, D and E,
wherein in order to calculate a position of the unknown point B or A, a vector between points D and E is displaced parallel to itself so that, starting from the non-invasively determined point A or B, the displaced vector points towards the unknown point B or A, a length of the displaced vector is multiplied by a factor that increases the displaced vector, and a tip of the thus increased displaced vector is assumed as a position of the unknown point B or A.

5. A method in accordance with claim 4, wherein the factor has a fixed value.

6. A method in accordance with claim 5, wherein the factor is between 2.8 and 2.5.

7. A method in accordance with claim 6, wherein in males the factor is between 2.8 and 2.75.

8. A method in accordance with claim 6, wherein in females the factor is between 2.63 and 2.58.

9. A method in accordance with claim 4, wherein the factor is determined by a distance vector of the non-invasively determined point A or B and point C being projected onto the displaced vector, and by a projected distance along the displaced vector being double.

10. An apparatus configured to determine a pelvic inlet plane of a pelvic bone, the pelvic inlet plane being defined by the following three points of the pelvic bone:
point A denoting a left anterior superior iliac spine; point B denoting a right anterior superior iliac spine; and point C denoting a pubic symphysis,
the apparatus comprising:
a navigation system,
a navigated position sensor configured for detection of each of the points A, B and C and for detection of the following further points:
point D denoting a left posterior superior iliac spine; and
point E denoting a right posterior superior iliac spine, and
a data processor configured to calculate a position of the pelvic inlet plane from position data of point A or B and of points C, D and E,
the navigated position sensor being configured to determine one of the two points A and B non-invasively and the other of the two points B or A being unknown;
the navigated position sensor being configured to determine all of points C, D, and E non-invasively; and
the data processor being configured to calculate the position of the pelvic inlet plane by:
displacing a vector between points D and E parallel to itself so that it passes through the non-invasively determined point A or B, and
calculating the pelvic inlet plane as the plane which is defined by a vector between the non-invasively determined point A or B and point C and by the displaced vector starting from the non-invasively determined point A or B which runs parallel to the vector between points D and E.

11. An apparatus in accordance with claim 10, wherein the position sensor is a palpation instrument.

12. An apparatus in accordance with claim 10, wherein the position sensor is an ultrasonic sensor.

13. An apparatus configured to determine a pelvic inlet plane of a pelvic bone, the pelvic inlet plane being defined by the following three points of the pelvic bone:
point A denoting the left anterior superior iliac spine; point B denoting the right anterior superior iliac spine; and point C denoting the pubic symphysis,
the apparatus comprising:
a navigation system,
a navigated position sensor configured for detection of each of the points A, B and C and for detection of the following further points:
point D denoting the left posterior superior iliac spine; and
point E denoting the right posterior superior iliac spine, and
a data processor configured to calculate a position of the pelvic inlet plane from position data of point A or B and points C, D and E,
the navigated position sensor being configured to determine one of the two points A and B non-invasively and the other of the two points B or A is unknown;
the navigated position sensor being configured to determine all of points C, D, and E non-invasively; and
the data processor being configured to calculate the position of the pelvic inlet plane by:
displacing a vector between points D and E parallel to itself so that, starting from the point A or B, the displaced vector points towards the unknown point B or A,
multiplying a length of the displaced vector by a factor that increases the displaced vector, and
assuming a tip of the thus increased displaced vector as a position of the unknown point B or A.

14. An apparatus in accordance with claim 13, wherein the factor has a fixed value.

15. An apparatus in accordance with claim 14, wherein the factor is between 2.8 and 2.5.

16. An apparatus in accordance with claim 15, wherein in males the factor is approximately between 2.8 and 2.75.

17. An apparatus in accordance with claim 15, wherein in females the factor is between 2.63 and 2.58.

18. An apparatus in accordance with claim 13, wherein the factor is determined by a distance vector of the determinable point A or B and point C being projected onto the displaced vector, and by a projected distance along the displaced vector being doubled.

* * * * *